(12) United States Patent
Kravets

(10) Patent No.: US 8,962,527 B2
(45) Date of Patent: Feb. 24, 2015

(54) PROCESS FOR PREPARATION OF HERBICIDAL SALTS

(75) Inventor: Eduard Kravets, Hampton (AU)

(73) Assignee: Nufarm Australia Limited, Laverton North, Victoria (AU)

( * ) Notice: Subject to any disclaimer, the term of this patent is extended or adjusted under 35 U.S.C. 154(b) by 0 days.

(21) Appl. No.: 13/698,470

(22) PCT Filed: May 11, 2011
(Under 37 CFR 1.47)

(86) PCT No.: PCT/AU2011/000550
§ 371 (c)(1),
(2), (4) Date: Jun. 26, 2013

(87) PCT Pub. No.: WO2011/143690
PCT Pub. Date: Nov. 24, 2011

(65) Prior Publication Data
US 2013/0316907 A1    Nov. 28, 2013

Related U.S. Application Data

(60) Provisional application No. 61/345,192, filed on May 17, 2010.

(51) Int. Cl.
| | | |
|---|---|---|
| C07C 51/41 | (2006.01) | |
| C07D 295/06 | (2006.01) | |
| C07D 213/807 | (2006.01) | |
| A01N 43/60 | (2006.01) | |
| A01N 37/40 | (2006.01) | |
| A01N 39/02 | (2006.01) | |
| A01N 39/04 | (2006.01) | |
| C07D 213/79 | (2006.01) | |
| C07D 213/803 | (2006.01) | |
| A01N 37/10 | (2006.01) | |

(52) U.S. Cl.
CPC ............... *C07C 51/41* (2013.01); *A01N 37/40* (2013.01); *A01N 39/02* (2013.01); *A01N 39/04* (2013.01); *C07C 51/412* (2013.01); *C07D 213/79* (2013.01); *C07D 213/803* (2013.01); *A01N 37/10* (2013.01); *A01N 43/60* (2013.01); *C07D 213/807* (2013.01); *C07D 295/06* (2013.01)
USPC ........... 504/235; 562/472; 562/474; 544/395; 546/310; 504/323; 504/324

(58) Field of Classification Search
None
See application file for complete search history.

(56) References Cited

U.S. PATENT DOCUMENTS

| | | | |
|---|---|---|---|
| 5,221,319 A | 6/1993 | Van Haften et al. | |
| 5,266,553 A | 11/1993 | Champion et al. | |
| 2005/0233904 A1* | 10/2005 | Hills et al. | 504/102 |
| 2008/0032892 A1 | 2/2008 | Linton | |

FOREIGN PATENT DOCUMENTS

| | | |
|---|---|---|
| GB | 1301197 A | 12/1972 |
| WO | 2010/071936 A1 | 7/2010 |

OTHER PUBLICATIONS

Seth et al., "Studies on the Synthesis of Ammonium Salts of 2,4-dichlorophenoxyacetic Acid (2,4-D) to Enhance its Bioregulating Potential," J. Indian Chem. Soc. 88:405-411 (2011) (English abstract only).
PCT International Search Report for PCT/AU2011/000550, dated Jul. 8, 2011.

* cited by examiner

*Primary Examiner* — Richard Schnizer
*Assistant Examiner* — Katherine Peebles
(74) *Attorney, Agent, or Firm* — LeClairRyan, a Professional Corporation

(57) ABSTRACT

A process for the preparation of solid amine salts of aromatic substituted carboxylic acid herbicides by reaction of the aromatic substituted carboxylic acid herbicide with an amine comprising reacting the aromatic substituted carboxylic acid herbicide in an ether solvent with an amine to form the amine salt and collecting the amine salt of the aromatic substituted carboxylic acid herbicide as a precipitate from the ether solvent reaction mixture wherein the ether is a dialiphatic ether comprising at least one primary aliphatic group.

17 Claims, No Drawings

PROCESS FOR PREPARATION OF HERBICIDAL SALTS

This application is a national stage application under 35 U.S.C. §371 of PCT Application No. PCT/AU2011/000550, filed May 11, 2011, which claims the priority benefit of U.S. Provisional Patent Application Ser. No. 61/345,192, filed May 17, 2010.

FIELD OF THE INVENTION

This invention relates to a process for the preparation of herbicidal carboxylate salts and in particular herbicidal aromatic carboxylate salts formed with an amine neutralising base.

BACKGROUND

Aromatic carboxylic acid herbicides such as aryl substituted carboxylic acid herbicides and aryloxy substituted acid herbicides have been used for many years. Many such herbicides are particularly useful in selectively controlling broad leaf vegetation. These aromatic carboxylic acids are generally converted to the ester form or the salt form to improve solubility in suitable solvents. The ester and salt forms of many of the herbicides are commercially available and sold either as a liquid concentrate to be diluted with water prior to use or as an aqueous solution. The ester forms are generally available as an organic solvent based emulsifiable concentrate. The salts, on the other hand are water soluble and available as an aqueous solution or solid.

Champion et al (U.S. Pat. No. 5,266,553) describes a method of manufacture of a dry water soluble salt composition which involves the use of a solvent comprising water as a major component. This process has a high energy consumption requirement and in order to minimise decomposition of the salt product sophisticated equipment is required to remove water at low temperature. Some salts, particularly 2,4-D dimethyl amine (DMA) salt, have been prepared using acetone as a solvent. In this process the 2,4-D is dissolved in acetone and the acetone solution is saturated with DMA. The 2,4-D DMA salt precipitates on formation and may be isolated by filtration and dried.

The formation of the salt in a solvent such as acetone also has significant problems which reduce the efficacy and economic viability of the process. While the salts are insoluble in acetone the presence of water significantly increases solubility so that as much as 10% of the product may remain dissolved.

Impurities are also formed in acetone. These include mesityl oxide and diacetone alcohol which must be purged from the system. These impurities also reduce the amount of solvent which can be reused. This significantly reduces product yield and produces a waste disposal problem. As a result isolation of useful materials from the waste stream is difficult and when the raw materials are relatively expensive, such as MCPP and Dicamba the process is uneconomical. Furthermore, some phenoxy acids such as MCPP can not be used because the resulting salts (e.g. MCPP/DMA) are too soluble in acetone.

There is a need for a process for preparing salts of substituted carboxylic acid herbicides in which the yield is high, the formation of impurities is minimised and the product can be easily isolated in solid form.

SUMMARY OF THE INVENTION

The invention provides a process for the preparation of solid amine salts of aromatic substituted carboxylic acid herbicides by reaction of the aromatic substituted carboxylic acid herbicide with an amine comprising reacting the aromatic substituted carboxylic acid in the ether solvent with an amine to form the amine salt and collecting the amine salt of the aromatic substituted carboxylic acid herbicide as a precipitate from the ether solvent reaction mixture wherein the ether is a dialiphatic ether comprising at least one primary aliphatic group.

Preferably the ether solvent is of formula $R_3OR^1$ wherein R is primary alkyl, such as methyl, ethyl and n-propyl;

$R^1$ is selected from $C_3$ to $C_6$ alkyl and preferably selected from the group consisting of n-propyl, isopropyl, n-butyl, isobutyl, tert-butyl and isoamyl.

Specific examples of preferred ethers include methyl tert-butyl ether, ethyl tert-butyl ether, isopropyl methyl ether and isoamyl methyl ether. Generally it is preferred that R is methyl. The most preferred ether is methyl tert-butyl ether. The most preferred ethers have a boiling point of no more than 70° C. and preferably from 40° C. to 70° C.

The amine is preferably selected from the group consisting of ammonia, alkyl amines, dialkylamines, trialkylamines, alkanolamines, dialkanolamines and trialkanolamines and mixture thereof.

The alkyl portions of the alkyl amines and alkanolamines are preferably each $C_1$ to $C_4$ alkyl and more preferably are methyl or ethyl or mixture thereof. Thus the preferred amines are $C_1$ to $C_4$ alkylamine, di-($C_1$ to $C_4$ alkyl)amines, tri-($C_1$ to $C_4$ alkyl)amines, $C_1$ to $C_4$ alkanol amines and di-($C_1$ to $C_4$ alkanol)amines and tri-($C_1$ to $C_4$ alkanol)amines. The more preferred amines are selected from the group consisting of ammonia, dimethylamine, ethylamine, diethylamine, triethylamine, ethanolamine, diethanolamine, triethanolamine, monoisopropylamine and diisopropylamine.

The preferred aromatic carboxylic acid herbicides include (a) aryl substituted carboxylic acid herbicides and (b) aryloxyalkanoic acid herbicides.

The preferred aryl carboxylic acid herbicides are selected from benzoic acid and pyridine acid (picolinic acid) herbicides. The preferred aryl carboxylic acid herbicides are selected from the group consisting of 2-methoxy-3,6-dichlorobenzoic acid (dicamba), 3,5,6-trichloro-o-anisic acid (tricamba), 1-napthaline acetic acid, 3-amino-2,5-dichlorobenzoic acid (amiben), 2,3,5-triiodobenzoic acid, trichlorobenzoic acid and 2,4,6-trichlorophenyl acetic acid (fenac).

The preferred picolinic acid herbicides are selected from dichloropicolinic acid particularly 3,6-dichloropicolinic acid (clopyralid), and 4-amino-3,5,6-trichloropicolinic acid (picloram).

The preferred aryloxyalkanoic acid herbicides include pyridyloxy alkanoic acids such as trichloropyridyloxyacetic acid (trichlopyr); polynuclear aryloxy alkanoic acids such as 2-napthoxypropionic acid and phenoxyalkanoic acid herbicide such as those of formula II:

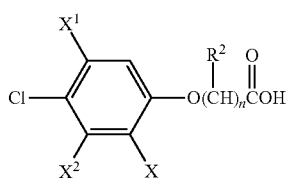

wherein X and $X^1$ are independently selected from halogen (preferably chloro) and methyl;

$X^2$ is hydrogen or amino (preferably hydrogen);
$R^2$ is hydrogen or methyl; and
n is 1, 2 or 3.

Still more preferred aryloxy alkanoic acids are selected from the group consisting of 2,4-dichlorophenoxyacetic acid (2,4-D), 4-(2,4-dichlorophenoxy)-butyric acid (2,4-DB), (RS)-2-(2,4-dichlorophenoxy)propionic acid (dichlorprop), (R)-2-(2,4-dichlorophenoxy)propionic acid (dichlorprop-P), (±)-2-(2,4,5 trichlorophenoxy)propionic acid (fenoprop), 4-chloro-o-tolyloxy-acetic acid (MCPA), 4-(4 chloro-o-tolyloxy)butyric acid (MCPB), (RS)-2-(4-chloro-o-tolyloxy)propionic acid (mecoprop), (R)-2-(4-chloro-o-tolyloxy)butyric acid (mecoprop-P) and 3,5,6-trichloro-2-pyridyloxyacetic acid, (triclorpyr).

The more preferred aromatic substituted carboxylic acids for use in the present invention are selected from the group consisting of 2,4-D, 2,4-DB, Dicamba, dichlorprop, dichlorprop-P, fenoprop, MCPA, MCPB, mecoprop, mecoprop-P, trichloropyr and picloram.

The use of the specific ethers in accordance with the invention provides high solubility of the acid and insolubility of the amine salt product. Further, while many workers have considered ethers to be dangerous to work with due to the potential for formation of peroxides, we have found that the ethers used in the process of the invention remain inert throughout the reaction avoiding the build up of impurities. Moreover, the ethers can be readily removed from the reaction product by evaporation at low temperatures (ie less than about 60° C.).

It is a significant advantage of the process of the invention that the product may be precipitated from the ether and collected and the mother liquor recycled for use as the reaction solvent for further preparation of amine salts products. We have found that a recycle of this type is only possible to a limited extent with solvents such as acetone which have been previously used due to the tendency of these solvents to concentrate impurities in the waste stream. Accordingly purging of impurities from the waste stream which is necessary for solvents such as acetone can essentially be eliminated with the process of the present invention thereby reducing waste.

A further advantage of the present invention is that the efficiency of the process and the preparation of the ethers allows formulation adjuvants to be added during the process of the invention. This allows the blending and formulation of the amine salt herbicide to be eliminated or significantly reduced.

The adjuvants may be added to the reaction mixture with the reagents or to the reaction mixture during or after the reaction. The preferred adjuvants for use in this way include water dispersible adjuvants. Examples of formulation additives which may be added to the reaction mixture include sequestering agents such as sodium lignosulfonates, casein, ethylenediamine tetraacetic acid (EDTA) and its salts, nitrilotracetic acid and its salts, ethylenediamine disuccinic acid (EDDS) and salts and one or more surfactants, such as octylphenol exthoxylates, nonylphenol ethoxylates, alcohol ethoxylates and alcohol ethoxylate/propoxylate copolymers, to assist dissolution of the salt in water and/or assist the spread of the spray solution on the sprayed surface.

The process of the invention involves the reaction of an aromatic substituted carboxylic acid herbicide with an amine in the presence of certain ethers as the reaction solvent. The volume of ether solvent required will depend on the solubility of the aromatic carboxylic acid starting material of interest under the reaction conditions used.

The reaction is preferably carried out at a temperature above 30° C. and more preferably above 35° C. The temperature will preferably be no more than 70° C. and under ambient conditions will depend on the boiling point of the ether solvent. The reaction between the aromatic carboxylic acid and amine is generally exothermic so that a significant increase in temperature occurs without the need for heating.

In many cases, for example with MTBE solvent, the exotherm is sufficient to increase the temperature to above the boiling point of the solvent and it is desirable to provide the reaction vessel with a reflux condenser. The aromatic acid is preferably reacted with an approximately equimolar amount of the amine although a slight excess may be desirable to eliminate or minimise residual acid. The amine is preferably added to a stirred mixture of the aromatic acid in the ether solvent. It will be appreciated that it is not necessary for the acid to be fully dissolved in the ether at the commencement of the reaction provided it progressively dissolves and reacts under the conditions provided during the reaction. Indeed we have found that in many cases it is desirable to use a concentration greater than required for complete solubility as the exotherm may be used to provide complete dissolution of a higher concentration under reaction conditions. This enables the use of solvent to be minimised.

The amine salt formed by neutralisation of the aromatic substituted carboxylic acid herbicide will generally be formed rapidly as a precipitate. The reaction may be monitored by simply adding small amounts of reaction mixture to water and observing (a) whether or not a precipitate is formed and (b) measuring the pH of the solution. The absence of precipitate in the aqueous phase and a persistent pH of at least 8 indicates that the reaction is completed and an excess of amine is present.

Where the temperature of the reaction residue is allowed to increase during the reaction the mixture is preferably cooled or allowed to cool to ambient temperature before collection of the precipitate. The precipitate may be collected by conventional means such as filtration or by centrifuging. Collection by centrifuging is preferred. The resulting product typically is preferably dried at a temperature of no more than 60° C.

As mentioned above it is an advantage of the present invention that the mother liquor of the collection process may be recycled. Preferably at least 90% of the mother liquor is recycled and more preferably essentially all of the mother liquor is recycled.

The invention will now be described with reference to the following examples. It is to be understood that the examples are provided by way of illustration of the invention and that they are in no way limiting to the scope of the invention.

EXAMPLES

The following general method of the invention was used in the processes of Examples 1 to 5.
General Method
Experimental Equipment and Procedure Round bottom 500 ml 3 neck flask equipped with stirrer, dip tube (for introduction of DMA) and thermometer.

The flask was charged with 300 ml of MTBE (or MTBE mother liquor from previous run) phenoxyacid (about 80 g) was added to the MTBE and the mixture stirred. Anhydrous DMA was then introduced with continued stirring. During the introduction of DMA the salt precipitates.

The reaction was monitored by addition of small amounts of reaction mixture to water. When the mixture provides a pH of 8 and remains at this pH the reaction was considered complete. The product was filtered and dried at temperature not greater than 60° C. The mother liquor is made up with fresh MTBE, ready for the next batch.

Experimental Results

Example 1

MCPA/DMA Salt

MCPA tech grade was supplied by Nufarm, Holland.
The finished product had the following characteristics:
 Assay 810 g/kg (average)
 PH 5.5-6.5 (3% solution in $H_2O$)
MCPA content in mother liquor <1%. Product is extremely hydroscopic.

Example 2

Dicamba/DMA Salt

Dicamba tech grade was supplied by Novataris.
The finished product had the following characteristics:
 Assay 800 g/kg (average)
 pH 5.5-6.5 (3% solution in $H_2O$)
Dicamba content in mother liquor was <1%. Product is extremely hydroscopic.

Example 3

MCPP/DMA Salt

MCPP tech is supplied by Nufarm, Holland.
Finished product:
 Assay 810 g/kg (average)
 pH 5.8-6.3 (3% solution in $H_2O$)
MCPP content in mother liquor <1%. Product is extremely hydroscopic.
NB—This product cannot be made using any other solvent.

Example 4

2,4-DP/DMA Salt 2,4-DP tech is supplied by Nufarm, Holland.
Finished product:
 Assay 807 g/kg (average)
 PH 5.8-6.5 (3% solution in $H_2O$)
2,4-DP content in mother liquor <1%. Product is not hydroscopic.

Example 5

In Situ Formation of Broad Leaf Weader Based on DMA Salts of MCPA, MCPP and Dicamba MCPA, MCPP and Dicamba were added in a mass ratio of 1.8:8:1 to the TBME
REAX.83.A (sodium lignosulfonate sequencing agent) 2% of mass of acids and 1% EDTA as disodium salt were added.
The mixture was stirred until the acid mixture was completely dissolved. DMA was introduced and the product precipitated. The product was filtered and dried. The product passed stability tests with 3 WHO water 0° C. After 24 hours in refrigerator, no precipitate was observed. Five batches of recycled mother liquor were prepared and all products passed stability test.
pH level is 5.5-6.5 (3% solution in $H_2O$).

Total acids content in mother liquor <1%. Formulation is hydroscopic.

Example 6 and Comparative Example A

The following raw materials were used:
1. 2,4-D (tech)
2,4-D (tech.) was manufactured by Nufarm Limited (Laverton) (Bag No. 6080).
The batch had the following composition (% w/w):

| | |
|---|---|
| moisture | 0.72 |
| 2,4-D | 98.32 |
| 2-chlorophenoxyacetic acid | 0.14 |
| 4-chlorophenoxyacetic acid | 0.15 |
| 2,6-D | 1.15 |
| 2,4,6-T | 0.04 |
| 2,4-DCP | 0.20 |
| NaCl | 0.31 |

2. DMA (anhydrous) was supplied in 60 liter bottle by Nufarm WA (Kwinana).
3. MTBE (99%) was supplied by Aldrich.
4. Morewet (REAX83A) was supplied by Westvaco Polychemicals department.
5. EDTA (acid form) was supplied by Ajax Chemicals.
This Example compares the preparation of 24-D/DMA salt using acetone as the solvent (comparative Example A) and a process of the invention in which MTBE is used as the reaction solvent.

Comparative Example A Process

DMA (807 kg) was pumped into a reaction vessel equipped with a stirrer and containing a solution of 2,4-D 4,000 kg to recycled acetone mother liquor to yield a total volume of 1200 liters.
The temperature was maintained at about 25° C. to 30° C. and 2,4-D dimethylamine salt formed as a precipitate.
The product was collected in a centrifuge and the mother liquor recycled. It was found that as a result of build up of impurities in the mother liquor it was necessary to purge a proportion of recycle resulting in loss of a significant proportion of product. The presence of product in the mother liquor (about 10% of total product) also necessitated that acetone be removed by distillation.

Example 6

Process

MTBE was charged into a reactor equipped with the overhead reflux condenser and a stirrer. The phenoxyacid, REAX83 and EDTA were added. The mixture was stirred for 15-20 minutes. Anhydrous DMA was added till solution reaches and remained at pH of above 8. During introduction of DMA, the reaction temperature rose to the boiling point of the MTBE (56° C.). Product precipitation occurred during introduction of DMA. The resulting product slurry was cooled by water to 25° C. and the precipitate collected as a wet cake in a centrifuge. The wet cake from centrifuge was dried in a drier while the mother liquor was recycled to the reactor for next batch. Fresh MTBE was added to the reactor to compensate for MTBE losses.

CONCLUSION

Table 1 below provides comparison for the ether and acetone processes.

TABLE 1

|  | CE-A (Acetone Process) | Example 6 (Ether Process) |
|---|---|---|
| 2,4-D (tech.) charge (kg) | 4,000 | 4,000 |
| (bags) | 5 | 5 |
| Reaction mass (kg) | 14022 | 12829 |
| S.G. of solvent, g/mL | 0.791 | 0.739 |
| Mass of dray final product (Yield) (Kg) | 4341 | 4875 |
| Isolated yield (%) | 92.5 | 100 |
| Active as 2,4-D (%) | 82.4 | 79.8 |
| Formulation in situ | Not Possible | Yes |

The invention claimed is:

1. A process for the preparation of solid amine salts of aromatic substituted carboxylic acid herbicides comprising:
   reacting the aromatic substituted carboxylic acid herbicide in an ether solvent with an amine to form the amine salt; and
   collecting the amine salt of the aromatic substituted carboxylic acid herbicide as a precipitate from the ether solvent reaction mixture;
   wherein the ether solvent is methyl tert-butyl ether, the aromatic substituted carboxylic acid herbicide is at least one selected from the group consisting of dicamba, 2,4-D, 2,4-DB, dichlorprop, dichlorprop-P, MCPA, MCPB, mecoprop, mecoprop-P, triclopyr, clopyralid and picloram, and the amine comprises at least one selected from the group consisting of $C_1$ to $C_4$ alkylamines, di-($C_1$ to $C_4$ alkyl)amines, and tri-($C_1$ to $C_4$ alkyl)amines.

2. The process according to claim 1 wherein the aromatic substituted carboxylic acid herbicide is dicamba.

3. The process according to claim 1 wherein the aromatic substituted carboxylic acid herbicide is clopyralid or picloram.

4. The process according to claim 1 wherein the aromatic substituted carboxylic acid herbicide comprises at least one selected from the group consisting of 2,4-D, 2,4-DB, dichlorprop, dichlorprop P, MCPA, MCPB, mecoprop, and mecoprop-P.

5. The process according to claim 1 wherein the product is precipitated from the methyl tert-butyl ether solvent and collected, and the mother liquor is recycled for use as the reaction solvent for further preparation of amine salt products.

6. The process according to claim 1 wherein a formulation adjuvant is added during the process.

7. The process according to claim 6 wherein at least one adjuvant is added to the reaction mixture with the reagents or to the reaction mixture during or after the reaction.

8. The process according to claim 6 wherein the adjuvant comprises at least one selected from the group consisting of sequestering agents, and one or more surfactants to assist dissolution of the salt in water and/or assist spreading of a spray solution on a sprayed surface.

9. The process according to claim 1 wherein the reaction is carried out at a temperature in the range of from 35° C. to 70° C.

10. The process according to claim 1 wherein the reaction mixture comprises a concentration of methyl tert-butyl ether less than required for complete solubility of the reactants at room temperature and the reactants become soluble during the process.

11. The process according to claim 1 wherein said collecting is carried out by centrifuging.

12. The process according to claim 1 wherein the amine is selected from the group consisting of dimethylamine, ethylamine, diethylamine, triethylamine, monoisopropylamine, and diisopropylamine.

13. The process according to claim 1 wherein the aromatic substituted carboxylic acid herbicide is selected from the group consisting of 2,4-D, MCPA, dicamba, mecoprop and mecoprop-P.

14. The process according to claim 1 wherein the aromatic substituted carboxylic acid herbicide is 2,4-D.

15. A process for the preparation of solid dimethyl amine salts of aromatic substituted carboxylic acid herbicides selected from the group consisting of dicamba, 2,4-D, dichlorprop, dichlorprop-P, MCPA, mecoprop, and mecoprop-P, the process comprising:
   reacting the aromatic substituted carboxylic acid herbicide in methyl tert-butyl ether solvent with the dimethyl amine; and
   collecting the dimethyl amine salt of the aromatic substituted carboxylic acid herbicide as a precipitate from the methyl tert-butyl ether solvent.

16. The process according to claim 15 wherein the aromatic substituted carboxylic acid herbicide is 2,4-D.

17. The process according to claim 15 wherein the aromatic substituted carboxylic acid herbicide is dicamba.

* * * * *